(12) United States Patent
Algawi et al.

(10) Patent No.: US 11,779,390 B2
(45) Date of Patent: Oct. 10, 2023

(54) PERICARDIUM CATHETER INCLUDING CAMERA FOR GUIDING CUTTING THROUGH PERICARDIUM

(71) Applicant: Biosense Webster (Israel) Ltd., Yokneam (IL)

(72) Inventors: Yehuda Algawi, Binyamina (IL); Assaf Govari, Haifa (IL); Ilya Sitnitsky, Nahariya (IL); Gili Attias, Haifa (IL); Israel Zilberman, Yokneam (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 873 days.

(21) Appl. No.: 16/232,127

(22) Filed: Dec. 26, 2018

(65) Prior Publication Data
US 2020/0205885 A1 Jul. 2, 2020

(51) Int. Cl.
*A61B 1/00* (2006.01)
*A61B 18/14* (2006.01)
(Continued)

(52) U.S. Cl.
CPC ...... *A61B 18/1492* (2013.01); *A61B 1/00082* (2013.01); *A61B 1/00096* (2013.01);
(Continued)

(58) Field of Classification Search
None
See application file for complete search history.

(56) References Cited

U.S. PATENT DOCUMENTS 4,862,874 A * 9/1989 Kellner ............ A61B 1/00082
600/116
4,984,563 A * 1/1991 Renaud ............ A61B 1/00082
600/106
(Continued)

FOREIGN PATENT DOCUMENTS

EP 2967524 A1 1/2016
WO 2007046860 A2 4/2007
(Continued)

OTHER PUBLICATIONS

EP 19218140.2-1113—Extended European Search Report dated Mar. 19, 2020.
(Continued)

*Primary Examiner* — Timothy J Neal
(74) *Attorney, Agent, or Firm* — Notaro, Michalos & Zaccaria P.C.

(57) ABSTRACT

A medical probe includes a shaft, a camera, a hollow cutting tool, and an inflatable balloon. The shaft is configured for insertion through a cut in a body of a patient, whereas the shaft includes a working vacuum channel running therethrough. The camera is fitted at a distal end of the shaft and is configured to provide images of a target tissue site in the body. The hollow cutting tool is for insertion over a guidewire in the working vacuum channel of the shaft, whereas the hollow cutting tool is configured to pierce the target tissue site under guidance of images taken by the camera. The inflatable balloon is configured to stabilize the distal end of the shaft, whereas the inflatable balloon is located proximally to the camera so as not to obstruct the images of the target tissue site.

4 Claims, 3 Drawing Sheets

(51) Int. Cl.
*A61B 1/05* (2006.01)
*A61B 1/06* (2006.01)
*A61B 1/313* (2006.01)
*A61B 17/00* (2006.01)
*A61B 18/00* (2006.01)

(52) U.S. Cl.
CPC .............. *A61B 1/05* (2013.01); *A61B 1/0661* (2013.01); *A61B 1/3132* (2013.01); *A61B 2017/00243* (2013.01); *A61B 2018/00392* (2013.01); *A61B 2018/00577* (2013.01); *A61B 2018/00791* (2013.01)

(56) References Cited

U.S. PATENT DOCUMENTS

| | | | |
|---|---|---|---|
| 5,591,137 A * | 1/1997 | Stevens | A61M 39/0613 604/296 |
| 5,716,389 A * | 2/1998 | Walinsky | A61N 1/06 600/374 |
| 5,823,955 A * | 10/1998 | Kuck | A61N 1/056 606/41 |
| 5,827,216 A | 10/1998 | Igo et al. | |
| 6,419,654 B1 * | 7/2002 | Kadan | A61B 17/3417 600/101 |
| 8,075,532 B2 * | 12/2011 | Kassab | A61M 60/857 604/176 |
| 2003/0229342 A1 | 12/2003 | Winston et al. | |
| 2004/0087831 A1 | 5/2004 | Michels et al. | |
| 2007/0010793 A1 | 1/2007 | Callas et al. | |
| 2008/0183080 A1 | 7/2008 | Abraham | |
| 2008/0214895 A1 * | 9/2008 | Campos | A61B 1/00089 600/129 |
| 2008/0306333 A1 | 12/2008 | Chin | |
| 2009/0187074 A1 | 7/2009 | Saadat | |
| 2010/0274129 A1 | 10/2010 | Hooven | |
| 2013/0027531 A1 | 1/2013 | Miyoshi et al. | |
| 2013/0190561 A1 * | 7/2013 | Oskin | A61B 1/00121 600/110 |
| 2013/0211513 A1 | 8/2013 | Rourke | |
| 2015/0073216 A1 * | 3/2015 | Papay | A61B 1/07 600/116 |
| 2015/0157381 A1 | 6/2015 | Ashton et al. | |
| 2016/0249978 A1 | 9/2016 | Lee et al. | |
| 2017/0319233 A1 * | 11/2017 | Fonger | A61B 1/07 |
| 2018/0338673 A1 * | 11/2018 | Krimsky | A61B 34/20 |

FOREIGN PATENT DOCUMENTS

| | | |
|---|---|---|
| WO | 2015/108941 A1 | 7/2015 |
| WO | 2017192897 A1 | 11/2017 |
| WO | 2018083599 A1 | 5/2018 |

OTHER PUBLICATIONS

European Examination Report for corresponding European patent application No. EP 19218140.2, dated Dec. 3, 2021.
European Examination Report for corresponding European patent application No. EP 19218140.2, dated Jul. 27, 2022.

* cited by examiner

PERICARDIUM CATHETER INCLUDING CAMERA FOR GUIDING CUTTING THROUGH PERICARDIUM

FIELD OF THE INVENTION

The present invention relates generally to minimally invasive probes, and particularly to minimally invasive cardiac probes.

BACKGROUND OF THE INVENTION

Various techniques for applying a minimally invasive treatment to an intrabody tissue have been proposed in the patent literature. For example, U.S. Patent Application Publication 2016/0249978 describes an apparatus and methods for pericardial access to perform a procedure therein. The apparatus includes a catheter including a tubular member comprising a proximal end, a distal end sized for introduction into a patient's body, an imaging assembly on the distal end, and a substantially transparent expandable member attached to the tubular member distal end. The imaging assembly is disposed within an interior of the expandable member, wherein the imaging assembly images tissue through a surface of the expandable member. The tubular member includes a drainage lumen communicating one or more drainage ports on the tubular member distal end proximal to the balloon for aspirating fluid from the patient's body. The catheter may be used to access a pericardial space and an ablation probe may be introduced through the catheter to treat heart tissue while fluid is infused and/or aspirated via the drainage ports.

As another example, U.S. Patent Application Publication 2008/0183080 describes an interventional medical device that incorporates an imaging system and is minimally invasive. The device is equipped with an anchoring portion that may be slidable and fixed in a predetermined position of its elongate body outside the human body. The device further includes deployable first and second balloons for also securing the device to an internal wall, for example, within a human body. The medical device can be in the form of a catheter, a sheath, or comprise interventional devices, particularly those suitable for minimally invasive procedures in the pericardium. The dual sealing/locking balloons may comprise a slidably moveable assembly for moving from a first position over an inflation channel to a second position over an inflation channel for separately inflating a distal balloon and then a proximal balloon to the patient's skin surface. Alternatively, the balloon assembly may be fixed over first and second inflation/deflation channels from the proximal end. The imaging system comprises one or more ultrasound transducers disposed proximate to the distal end and/or on the sides of an elongate body portion and so can be used to guide the device to a target area, guide the inflation of the deployable balloons and guide the performance of a procedure and/or provide visual access to a target area for performing a procedure via a plurality of lumens.

U.S. Pat. No. 5,827,216 describes a pericardiocentesis apparatus and method for accessing the pericardial Space. The invention consists of inserting a percutaneous tube whose tip has a hole which is positioned over and contacts the anterior pericardium. Introducing a vacuum within the tube forms a pericardial bleb within that hole. A guided needle within the tube is advanced to puncture the pericardial bleb while avoiding contact with the epicardium. A hollow filament or electrocardial lead or flexible guide wire within the needle can then be advanced into the pericardial cavity. The guide wire may be used to guide an intrapericardial catheter into the pericardial space for injection or infusion of selected therapeutic agents into the pericardial space to treat various heart and blood vessel diseases. Controlled drug release material(s) can be injected through the needle for the slow and/or sustained delivery of the therapeutic agents into the pericardial cavity.

SUMMARY OF THE INVENTION

An embodiment of the present invention provides a medical probe including a shaft, a camera, a hollow cutting tool, and an inflatable balloon. The shaft is configured for insertion through a cut in a body of a patient, whereas the shaft includes a working vacuum channel running therethrough. The camera is fitted at a distal end of the shaft and is configured to provide images of a target tissue site in the body. The hollow cutting tool is for insertion over a guidewire in the working vacuum channel of the shaft, whereas the hollow cutting tool is configured to pierce the target tissue site under guidance of images taken by the camera. The inflatable balloon is configured to stabilize the distal end of the shaft, whereas the inflatable balloon is located proximally to the camera so as not to obstruct the images of the target tissue site.

In some embodiments, the target tissue site includes a pericardium site and wherein the shaft is configured for insertion through a cut in a chest of the patient.

In some embodiments, the medical probe further includes a second probe, which is configured to be inserted via the working vacuum channel for treating a target tissue location, whereas the camera is additionally configured to provide images of treatment by the second probe.

In an embodiment, the second probe is also configured to serve as a deflectable guidewire for the medical probe. In another embodiment, the second probe includes an ablation catheter.

In some embodiments, the inflatable balloon is configured to stabilize both the medical probe and the second probe.

In some embodiments, the target tissue location includes a myocardium location.

There is additionally provided, in accordance with an embodiment of the present invention, a method including inserting, through a cut in a body of a patient, a medical probe including a shaft having a working vacuum channel running therethrough, a camera fitted at a distal end of the shaft, and an inflatable balloon located proximally to the camera. A hollow cutting tool is inserted over a guidewire via the working vacuum channel, for piercing the target tissue site under guidance of images taken by the camera. The guidewire is retracted. A second probe is inserted via the working vacuum channel. The balloon is inflated so as to stabilize the medical probe and the second probe. A target tissue location is treated using the second probe under guidance of the images taken by the camera.

The present invention will be more fully understood from the following detailed description of the embodiments thereof, taken together with the drawings in which:

DETAILED DESCRIPTION OF EMBODIMENTS

Overview

Figure 1:
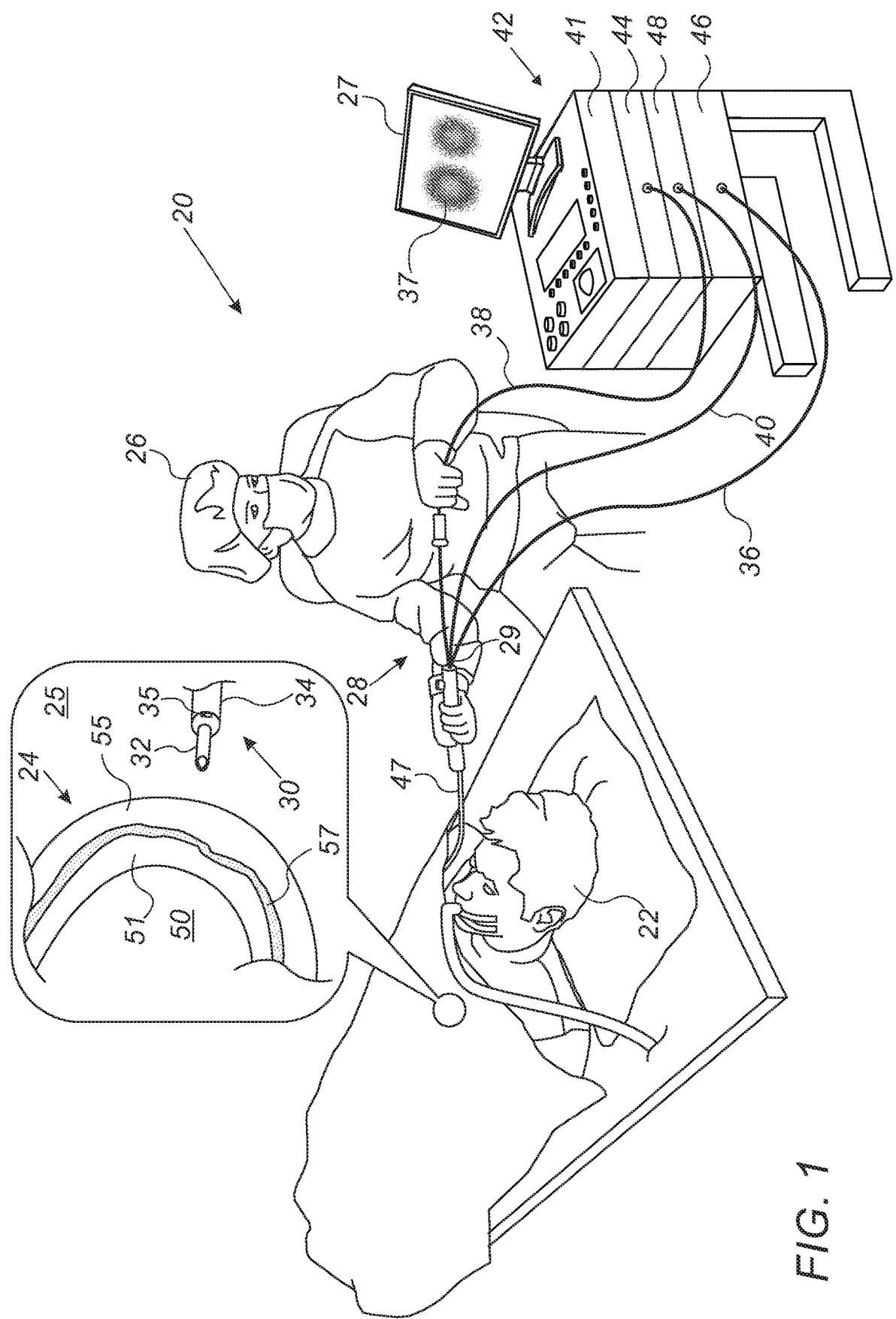
FIG. 1 is a schematic, pictorial illustration of a system for minimally invasive pericardial treatment comprising a pericardial catheter, in accordance with an embodiment of the present invention.

Pericardial treatment, such as radiofrequency (RF) ablation, may be used to alleviate heart problems, such as certain types of ventricular arrhythmias as well as some atrial fibrillations. However, pericardial ablation applied to an outer surface of the myocardium may have limited success, due in part to the presence of epicardial fat. The fat layer may prevent proper RF energy delivery by, for example, causing inadequate contact of the ablation catheter with muscle tissue. In addition, because of the existence of significant amounts of epicardial fat, any ablation energy that is intended for the myocardium may instead be absorbed by the fat, which has a substantially lower conductivity compared to the myocardium. Pericardial ablation may also be limited by increased likelihood of other complications, such that may arise because of energy delivery in close proximity to coronary vessels.

Embodiments of the present invention that are described and shown hereinafter provide a camera-guided medical probe (e.g., catheter, also referred herein as a "first probe") to enable controlled access and treatment of target tissue in the body, such as the myocardium. The embodiments described herein provide a camera-guided pericardium catheter comprising a second probe, which can access and treat the outer surface of the myocardium. The disclosed pericardium catheter is inserted into the patient through a small incision in the chest, and is navigated to the pericardium using the camera. Once the catheter is in position immediately outside the pericardium, the treating physician inserts a hollow cutting tool over a guidewire through a working channel of the catheter in order to, under guidance by images taken by the camera, pierce the pericardium, including piercing its fatty epicardial sub-layer. The camera assists the physician to avoid collateral damage in the process, such as accidently piercing the myocardium itself with the hollow cutting tool.

In the context of the disclosed description the term "hollow cutting tool" represents any tool that is inserted through a working channel of the pericardium catheter and used for performing a cut in the pericardium, e.g., a tool having a form of a needle, a blade or a cutting laser.

In some embodiments, the working channel additionally serves as a vacuum channel configured to lift the pericardium to facilitate its incision by the hollow cutting tool with minimum risk to the myocardium underneath.

The guidewire is than advanced through the incision in the pericardium and the hollow cutting tool is withdrawn, and the catheter is pushed over the guidewire through the incision in the pericardium. Once catheter is inside the pericardium, the guidewire retracted and the second probe, typically an RF ablation catheter, is inserted into the working channel and, again using the camera, is navigated to a desired region, such as a target body tissue (i.e., myocardium) location.

In some embodiments, the medical probe comprises an inflatable balloon, which is typically used during the subsequent ablation procedure and kept collapsed during incision. The balloon is typically located proximally to the camera, so as not to obscure a field of view comprising a forward line of sight (e.g., a cone of sight) between the camera and target tissue site (i.e., pericardium) for the incision. Subsequently, when inflated, the balloon stabilizes the pericardial catheter and the second probe by pushing against the epicardium layer from one end of the balloon and the myocardium from the other end.

In an embodiment, the pericardium catheter is constructed to be more flexible than the second probe, whereas the second probe can be deflected, so that the second probe, in addition to performing its treatment function (e.g., RF ablation), acts as a deflectable guidewire.

The disclosed camera-guided pericardium catheter may decrease risks of a minimally invasive pericardial treatment as well as potentially improving the clinical outcome of myocardium treatment, such as ablation.

System Description

FIG. 1 is a schematic, pictorial illustration of a system 20 for minimally invasive pericardial treatment comprising a pericardial catheter 28, in accordance with an embodiment of the present invention. A physician 26 inserts a shaft 29 of pericardial catheter 28 through a sheath 47 into the thorax of a patient 22, in the vicinity of a heart 24, through a cut in the chest of patient 22. Then physician 26 manipulates the pericardial catheter so that a distal end 30 of shaft 29 of the catheter, seen in inset 25, approaches pericardial sac 55 and cuts through it to access myocardium 51. The cut is made for the purpose of subsequently inserting a second, treatment probe, such as an ablation catheter to ablate the area underneath myocardium 51.

In order to obtain access to myocardium 51, distal end is fitted with a hollow cutting tool 32, which is advanced distally through a working channel in pericardial catheter 28. However, as noted above, cutting through pericardium sac 55, and in particular a fatty epicardium sub-layer 57 of pericardium sac 55, may result in collateral damage, such as hollow cutting tool 32 puncturing myocardium 51 and even penetrating into a cardiac cavity 50.

In order to carefully and accurately guide hollow cutting tool 32, physician 26 uses a camera 35, which is located at distal end 30, more particularly at the distal end of camera-supporting catheter 49, to provide an image 37 (e.g., video image) of pericardium 55 during the cutting procedure. The video image of pericardium 55 is presented to physician 26 on a display 27. To clear the field of view of camera 35, for example from blood, an irrigation pump 48 supplies fluid, such as saline solution, that washes the lens of camera 35. The clearing fluid flows via a lumen in catheter 28 to distal end 30 and exits from a tube 40.

As an additional means to avoid collateral damage, such as puncturing myocardium 51, physician 26 operates a vacuum channel 34, so as to lift the epicardium off of the myocardium, as described below. Channel 34 is connected to a vacuum pump 46 in console 24 via a cable tube 36.

After performing the cut in pericardium 55, hollow cutting tool 32 is retracted and a second probe, such as an ablation catheter (seen in FIG. 3) is advanced through the same, or a different, working channel of pericardial catheter 28, as described below, to treat myocardium 51.

In an embodiment, the ablation catheter is inserted, under the guidance of camera 35, through the pericardium cut in the vicinity of a myocardium location for ablation. After verifying that the ablation catheter tip is in contact with the myocardium at the targeted myocardium location, by using images captured by camera 35, physician 26 performs the RF ablation.

For performing the RF ablation, physician 26 actuates an RF energy generator 44 in a control console 42 to supply RF energy via a cable 38 to distal end 30. A temperature sensor (not shown in the figures) in distal end 30 may provide feedback to console 42 for use in controlling the RF energy dosage and/or flow rate of cooling irrigation.

Pericardium Catheter Including Camera for Guiding Cutting Through Pericardium

Figure 2:
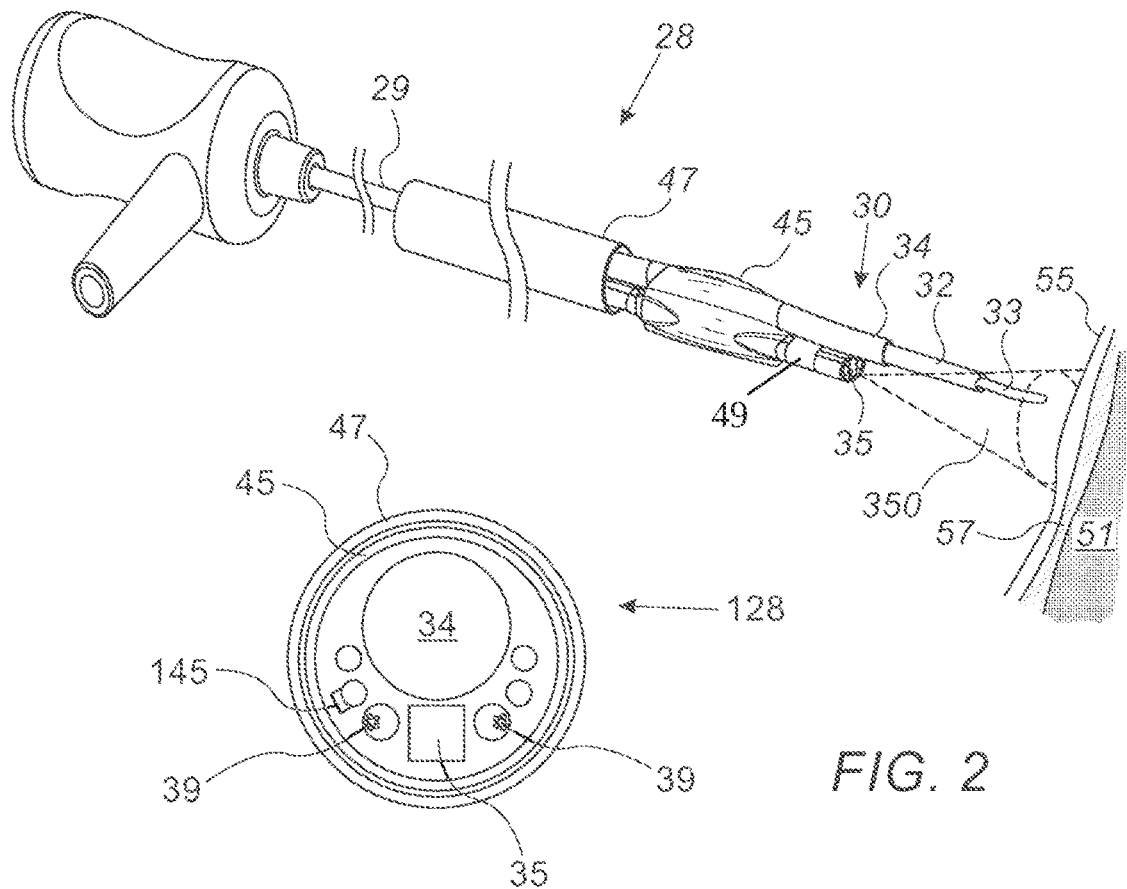
FIG. 2 is a schematic, pictorial illustration of the pericardial catheter of FIG. 1, in accordance with an embodiment of the present invention.

FIG. 2 is a schematic, pictorial illustration of the pericardial catheter 28 of FIG. 1, in accordance with an embodiment of the present invention. As seen, hollow cutting tool 32 protrudes beyond the distal edge of distal end 30, and is seen in proximity to pericardium sac 55 and epicardium layer 57 underneath. Hollow cutting tool 32 is inserted through vacuum channel 34 that serves also as a working channel (seen in a cross-section 128 of catheter 28). Vacuum channel 34 is configured to lift both layers 55 and 57 to facilitate their incision by hollow cutting tool 32 with minimum risk to myocardium 51 located underneath. The entire incision process is guided using camera 35 having a cone of sight 350 to provide images of hollow cutting tool 32 in relation to target pericardium tissue. Illumination to camera 35 is provided by one or more light sources 39, such as fiber optics bundles, or LEDs covered with diffusive optics.

An inflatable balloon 45, seen collapsed, is fitted distally to camera 35, so as not to block cone of sight 350. The balloon is subsequently inflated and collapsed using a fluid channel 145.

The example illustration shown in FIG. 2 is chosen purely for the sake of conceptual clarity. FIG. 2 shows only parts relevant to embodiments of the present invention. Other system elements, such as additional sensors fitted over distal end 30 are omitted. Catheter 28 may also include several additional working channels.

Figure 3:
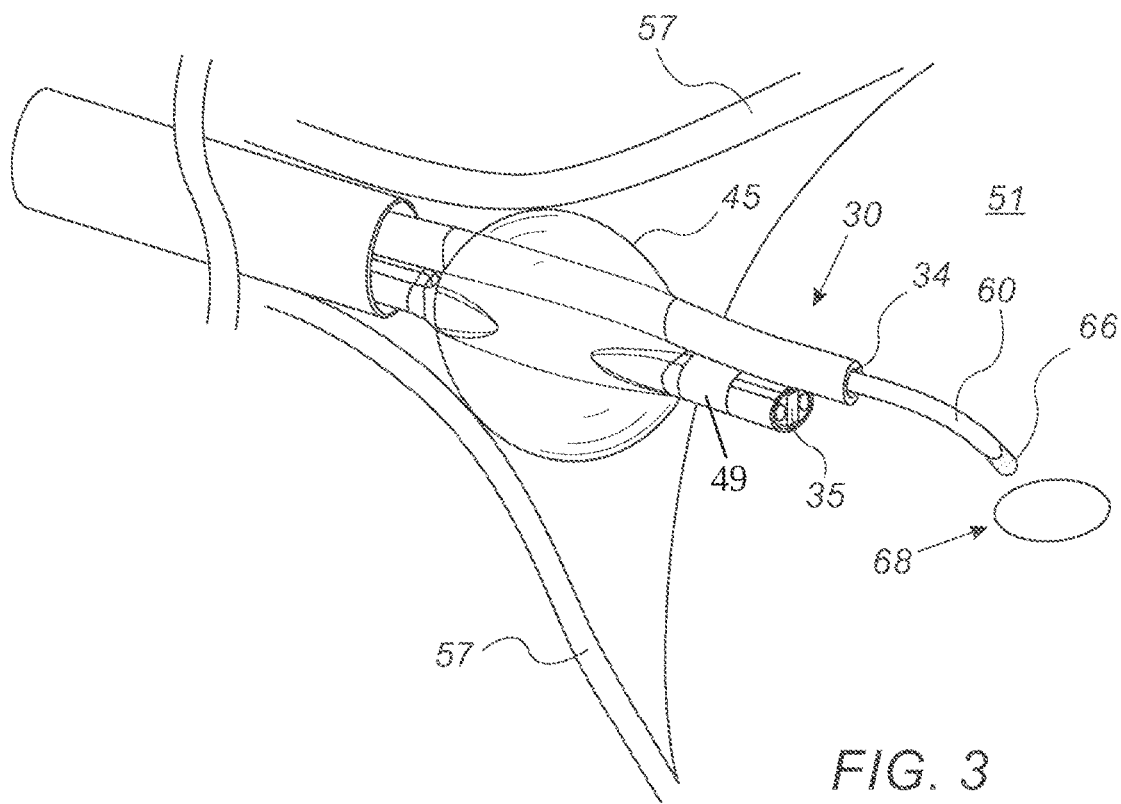
FIG. 3 is a schematic, pictorial illustration of a distal end of the pericardial catheter of FIG. 2, in accordance with an embodiment of the present invention.

FIG. 3 is a schematic, pictorial illustration of distal end 30 of the pericardial catheter of FIG. 2, in accordance with an embodiment of the present invention. As seen, an ablation catheter 60 having an ablation electrode 66 is inserted via vacuum/working channel 34, in order to ablate target tissue 68 over myocardium 51. Ablation catheter 60 is further configured to serve as a deflectable guidewire for catheter 28. Balloon 45 is inflated to stabilize catheters 28 and 60 during the procedure (e.g., by stabilizing distal end 30 of shaft 29). Camera 35 provides visual images of electrode 66 in relation to target myocardium location 68 to guide the RF ablative treatment.

The example illustration shown in FIG. 3 is chosen purely for the sake of conceptual clarity. Other system elements, such as another type of second probe, such as for infusion of medication, may be inserted through a working channel. Irrigation may be applied during ablation to target myocardium location 68 through another channel in pericardium catheter 28.

Figure 4:
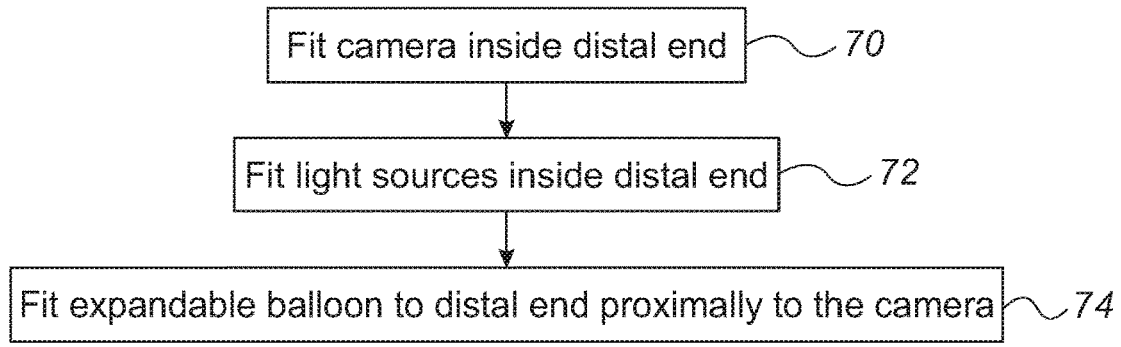
FIG. 4 is a flow chart that schematically illustrates a method for manufacturing the distal end of FIG. 3, in accordance with an embodiment of the present invention.

FIG. 4 is a flow chart that schematically illustrates a method for manufacturing distal end 30 of FIG. 3, in accordance with an embodiment of the present invention. The process begins with fitting camera 35 to distal end 30, in a way that the camera has a free line of sight distally to the distal end, at a camera fitting step 70. Next, optical light sources 39 (e.g., illumination fiber bundles or LEDs) are fitted to distal end 39, at an optical fibers fitting step 72. Finally, expandable balloon 45 is fitted to distal end 30, proximally to camera 35, so as not to disrupt camera 35 line of sight.

The example flow chart shown in FIG. 4 is chosen purely for the sake of conceptual clarity. Only manufacturing steps relevant to embodiments of the present invention are shown.

Figure 5:
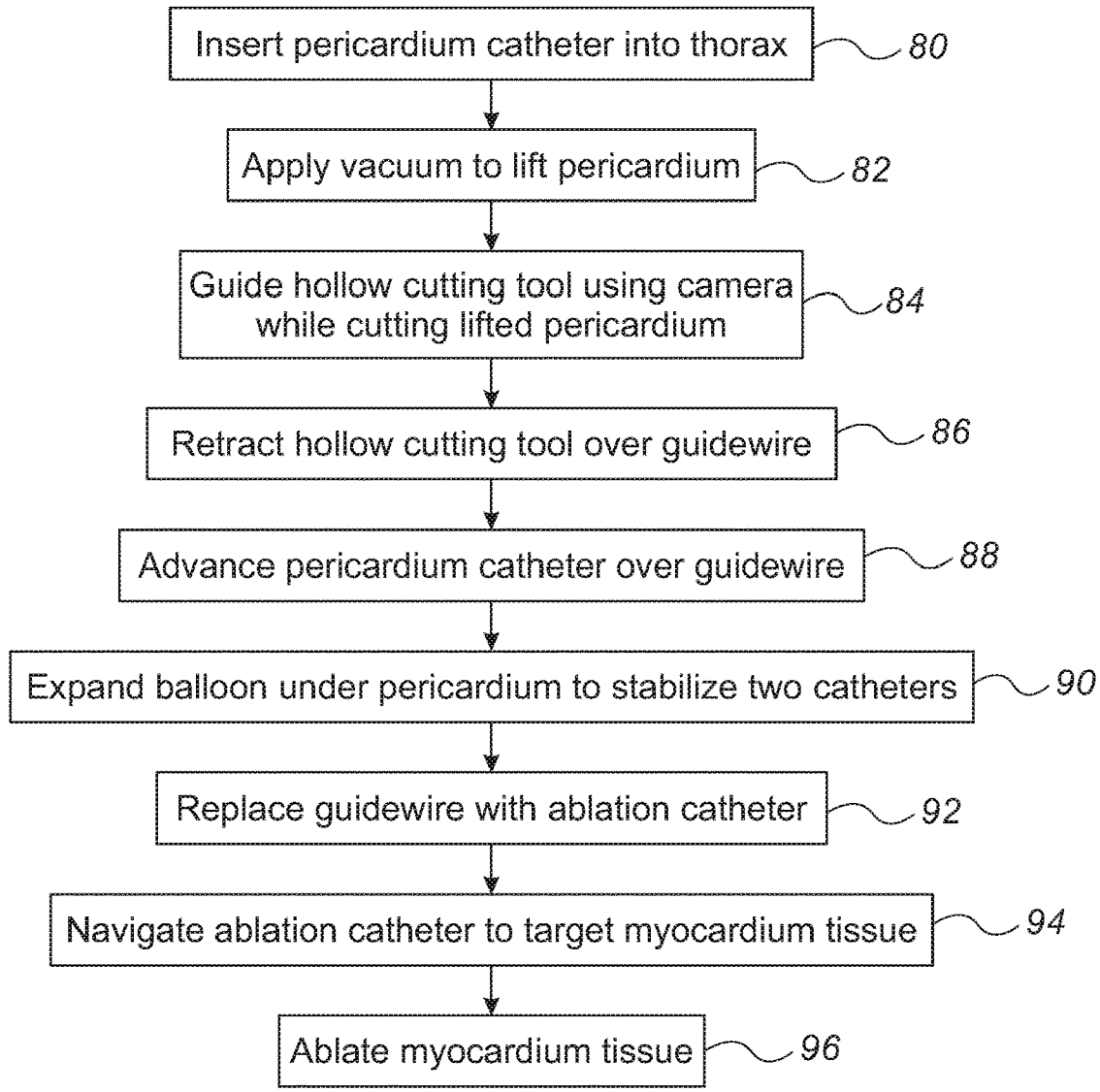
FIG. 5 is a flow chart that schematically illustrates a method for minimally invasive pericardial treatment, in accordance with an embodiment of the present invention.

FIG. 5 is a flow chart that schematically illustrates a method for minimally invasive pericardial treatment, in accordance with an embodiment of the present invention. The process begins with physician 26 inserting pericardium catheter 28 into the thorax of patient 22, to bring distal end 30 in the vicinity of heart 24, at a pericardium catheter insertion step 80. Next, physician 26 applies vacuum via channel 34, so as to lift pericardium sac 55 and epicardium sub-layer 57, at a pericardium lifting step 82. Using images that camera 35 provides, physician 26 applies hollow cutting tool 32 over guidewire 33 to cut the lifted pericardium, at a pericardium incision step 84.

At a cutting tool retraction step 86, physician 26 retracts hollow cutting tool 32 over guidewire 33.

Next, physician 26 advances distal end 30 over guidewire 33 to bring collapsed balloon 45 under epicardium sub-layer 57, at a pericardium catheter advancement step 88.

Once distal end 30 of catheter 28 is advanced sufficiently beyond the pericardium sac, physician 26 inflates balloon 45 to stabilize both catheters, at a balloon stabilizing step 90.

At a tool replacement step 92, physician 26 retracts guidewire 33 and inserts ablation catheter 60 through vacuum/working channel 34. Next, using camera 35, which has clear line of sight to myocardium 51, physician 26 navigates ablation catheter 60 to bring electrode 66 in contact with target myocardium 51 location 68, at an ablation catheter navigation step 96. Physician 26 may use catheter 60 as a deflectable guidewire to, if required, further slide over catheter 28, for example, to further stabilize the catheters. Finally, physician 26 ablates myocardium location 68, at an ablation step 96.

The example flow chart shown in FIG. 5 is chosen purely for the sake of conceptual clarity. In alternative embodiments, for example, physician 26 may additionally apply irrigation and measure tissue temperature.

Although the embodiments described herein mainly address cardiac applications, the methods and systems described herein can also be used in other applications, such as in minimally invasive camera guided surgery.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A dual-probe medical device, comprising:
a sheath;
a first probe, said first probe being a pericardium catheter, and a second probe, wherein said first probe is more flexible than said second probe, wherein said second probe is deflectable, wherein said second probe is designed to simultaneously perform radiofrequency ablation and function as a deflectable guidewire,
the first probe comprising a shaft positioned within the sheath, the shaft and the sheath configured for insertion through a cut in a body of a patient, wherein the shaft comprises a working vacuum channel running therethrough;
a camera, which is fitted at a distal end of a camera-supporting catheter disposed alongside the working vacuum channel, the camera configured to provide images of a target tissue site in the body;
a hollow cutting tool for insertion over a guidewire in the working vacuum channel of the shaft, wherein the hollow cutting tool is configured to pierce the target tissue site under guidance of images taken by the camera; and
an inflatable balloon disposed to completely surround both the working vacuum channel and the camera-supporting catheter in a circumferential direction and configured to fit within an internal circumference of the sheath while not inflated, the inflatable balloon located proximally to the camera so as not to obstruct the images of the target tissue site, wherein the inflatable balloon has a first and a second end, wherein the inflatable balloon specifically positioned, when inflated, to stabilize the pericardial catheter and the second probe by pushing against the epicardium layer from the first end of the inflatable balloon and the myocardium from the second end of the inflatable balloon circumferentially around the camera-supporting catheter and the working vacuum channel in an area adjacent to the inflatable balloon,
a lighting arrangement, consisting of two light sources, the two light sources being a first fiberoptic bundle and a second fiberoptic bundle, wherein the camera is flanked by the two light sources, wherein the first fiberoptic bundle is positioned on a right side of the camera and the second fiberoptic bundle is positioned on a left side of the camera,
wherein the camera is positioned beneath the working vacuum channel, and
wherein the working vacuum channel is configured to lift both a pericardium sac and an epicardium layer of a heart of the patient,
wherein the second probe is configured to be inserted via the working vacuum channel for treating a target tissue location, wherein the camera is additionally configured to provide images of treatment by the second probe.

2. The dual-probe medical device according to claim 1, wherein the target tissue site comprises a pericardium site and wherein the shaft is configured for insertion through a cut in a chest of the patient.

3. The dual-probe medical device according to claim 1, wherein the second probe comprises an ablation catheter.

4. The dual-probe medical device according to claim 1, wherein the target tissue location comprises a myocardium location.

\* \* \* \* \*